United States Patent [19]

Haug et al.

[11] Patent Number: 4,843,001

[45] Date of Patent: Jun. 27, 1989

[54] CONJUGATE FOR ENZYME IMMUNO DETERMINATIONS

[75] Inventors: Harald Haug, Peissenberg; Gerd Kleinhammer, Tutzing; Johann Mattersberger, Munich, all of Fed. Rep. of Germany

[73] Assignee: Boehringer Mannheim GmbH, Mannheim-Waldhof, Fed. Rep. of Germany

[21] Appl. No.: 884,431

[22] Filed: Jul. 11, 1986

[30] Foreign Application Priority Data

Jul. 19, 1985 [DE] Fed. Rep. of Germany ....... 3525911

[51] Int. Cl.$^4$ .................. G01N 33/53; C12Q 1/28; C12N 9/96
[52] U.S. Cl. .......................... 435/7; 435/28; 435/188; 435/810; 436/512
[58] Field of Search .................. 435/7, 188, 810, 4, 435/28; 436/512, 531, 532, 548

[56] References Cited

U.S. PATENT DOCUMENTS 4,410,633 10/1983 Hertl et al. ................. 436/500
4,486,534 12/1984 Albert et al. ................. 435/188

FOREIGN PATENT DOCUMENTS 0084807 3/1983 European Pat. Off. .

OTHER PUBLICATIONS

Nakane, P. K., and A. Kawaoi, J. of Histochem. Cytochem., vol. 22, No. 12, pp. 1084-1091 (1974).
Avrameas, S., T. Ternynck and J. L. Guesdon., Scand. J. Immunol., vol. 8, Suppl. 7, 7-23 (1978).

*Primary Examiner*—Robert J. Warden
*Assistant Examiner*—Toni R. Scheiner
*Attorney, Agent, or Firm*—Felfe & Lynch

[57] ABSTRACT

This invention teaches a process for preparing a conjugate useful in enzyme immunoassays, and the conjugate produced by the process. The process involves oxidizing an enzyme containing a carbohydrate portion, such as peroxidase, with periodic acid or an alkali metal salt thereof in an aqueous medium followed by reduction with sodium borohydride. The oxidation and reduction step may be carried out either before or after the enzyme is coupled to the immunologically effective component of the conjugate.

9 Claims, No Drawings

CONJUGATE FOR ENZYME IMMUNO DETERMINATIONS

The present invention is concerned with a conjugate suitable for enzyme immuno determinations and with a process for the preparation thereof.

Immunological detection methods have achieved outstanding importance for many analytical purposes but especially for clinical analyses because of their extraordinary sensitivity and specificity and have forced the purely chemical methods into the background. As a rule, in the case of these analysis processes, one of the immunological binding components is labelled, whereby, above all, radio-active labelling (RIA) initially and later enzyme labelling (EIA) have achieved outstanding importance.

Furthermore, in the scope of immunological detection processes with the use of enzyme labelling, a small number of enzymes has proved to be especially appropriate for labelling purposes, whereby easy determinability, high stability and the smallest possible influencing of the immune reaction are of decisive importance. Labelling enzymes which are already used or are usable include glucose oxidase (GOD) (E.C.1.1.3.4), $\beta$-fructosidase (invertase) (E.C. 3.2.1.26), alkaline phosphatase (AP) (E.C. 3.1.3.1) and peroxidase (POD) (E.C. 1.11.1.7), all of which contain a carbohydrate part in the molecule. They are used in the form of so-called enzyme conjugates. Hereunder are to be understood coupling products of the labelling enzymes with one of the immunologically effective reaction partners, whereby, as a rule, there is a covalent bond between the labelling enzyme and the immunological coupling component which, for example, can be an antigen, a hapten, an antibody or a derivative or fragment of an antibody.

It has now been found that admittedly in the case of the widely preponderating number of sera, in which a component of interest is determined by an EIA method with the use of such labelling enzymes and especially of POD as labelling enzyme, correct results are obtained when the results obtained are compared with those obtained with a corresponding RIA system. However, in the case of a certain number of sera, which hereinafter are called problem sera, there was observed a marked deviation from the correct values in the form of too highly positive results.

Therefore, it is an object of the present invention to overcome this disadvantage and to provide conjugates of labelling enzymes for enzyme immuno assays (EIA) which also provide correct results in the case of the so-called problem sera.

Thus, according to the present invention, there is provided a process for the preparation of a conjugate, suitable for enzyme immuno determinations, from a labelling enzyme, which contains a carbohydrate part, such as peroxidase, and an immunologically effective substance with the use of a coupling method acting on the protein part of the labelling enzyme, wherein, before or after coupling with the immunologically effective substance, the labelling enzyme is oxidised with periodic acid or with an alkali metal salt thereof in an aqueous medium and the oxidation product is then reduced with sodium borohydride.

Surprisingly, we have found that a periodate oxidation of the labelling enzyme molecule with subsequent reduction with sodium borohydride provides a labelling enzyme derivative which retains its enzymatic properties unchanged but also provides correct values with so-called problem sera which agree with the values obtained according to RIA methods.

The process of the present invention is, with regard to the pH values and the choice of appropriate buffers and buffer concentrations, carried out under the conditions known for the maintenance of the enzyme activity. In the case of POD, the oxidation step is preferably carried out at a pH value of from about 4 to 8.5, in buffered solution. The reduction is preferably carried out at a pH value of from about 7.5 to about 9. In any case, it is preferable to carry out the reaction with cooling, especially at temperatures below 10° C. and preferably of from 0 to 5° C. However, in principle, it is also possible, having regard to the known relatively good temperature stability of POD, also to work at higher temperatures of up to 37° C. For the other enzymes which can be used in the scope of the present invention, there apply the conditions with regard to pH value and temperature corresponding to their known properties.

Since the above-mentioned false results occur, above all, in the case of conjugates in which the enzyme is present attached with a hapten, it is assumed that the danger of false results exists especially when extreme size relationships are present between the labelling enzyme and its binding component, i.e. the latter, compared with the enzyme molecule, is very small. Typical examples of this include thyroxine ($T_4$) and triiodothyronine ($T_3$), i.e. low molecular weight hormonally effective haptens as binding component. Surprisingly, according to the present invention, it is possible to prevent falsely too high results although the size relationship of the two binding components in the conjugate remains unchanged, i.e. the large enzyme molecule, unchanged with regard to its small binding partner, can manifest a steric protective action.

The coupling of the enzymes can, in the scope of the process according to the present invention, be carried out before or after the oxidation-reduction treatment according to the present invention. A carrying out of the oxidation-reduction treatment according to the present invention after the preparation of the conjugate is, in particular, also possible when the immunologically effective binding component is itself a protein, for example TBG or an antibody or antibody fragment.

For the preparation of the labelling enzyme conjugate according to the present invention, there can be used the usual coupling methods, insofar as they themselves do not comprise an oxidation. Appropriate methods are described, for example in J. of Immunoassay, 4(3), 209–327/1983. Coupling methods with the use of bifunctional reagents which bring about a linking of amino groups or sulphhydryl groups are especially preferred. Preferred examples of such bifunctional reagents include N-succinimidyl-4-(N-maleimidomethyl)-cyclohexane-1-carboxylate (hinge method) and glutardialdehyde (Immunochem., 8, 1175–1179/1971). A direct condensation with the use of carbodiimide (J. Cell. Biol., 33, 307–318/1967) can also be employed. In general, as bifunctional bridge builders for the production of the linkage of the labelling enzyme with the ligand, there can also be used those according to the methods described in Federal Republic of Germany Patent Specifications Nos. 21 28 743 and 22 60 185, as well as, in general, hydroxysuccinimide derivatives.

As immunologically-active ligands, in the scope of the present invention, as already mentioned above, there can be used antibodies, fragments thereof, such as Fab, Fab$_2$, Fc fragments, chemically obtained derivatives of the antibodies or of their fragments, antigens and haptens, such as digoxin, digoxigenin, T$_3$, T$_4$, oestradiol, oestriol, progesterone, follate, theophylline, cortisol, phenobarbital and the like.

The following Table I shows the results of a T$_3$-enzyme immuno determination with the use of a conventional T$_3$-POD conjugate (conjugate I), of a T$_3$-POD conjugate obtained according to the present invention (conjugate II) and of radio-actively labelled T$_3$ (RIA) as reference method. A control serum is compared with 7 normal sera (NS) and 4 disturbed sera (DS; problem sera), human sera being used.

TABLE I

| sample | conjugate I (ng T$_3$/ml) | conjugate II (ng T$_3$/ml) | RIA (reference) |
|---|---|---|---|
| control serum | 1.42 | 1.36 | n.c. |
| NS 1 | 0.95 | 0.95 | n.c. |
| NS 2 | >6 | >6 | >6.00 |
| NS 3 | 3.58 | 3.93 | 4.12 |
| NS 4 | 2.96 | 3.10 | 3.10 |
| NS 5 | 2.08 | 2.32 | 2.39 |
| NS 6 | 2.31 | 1.96 | 2.02 |
| NS 7 | 1.44 | 0.91 | 0.75 |
| DS 1 | 7.43 | 0.92 | 1.25 |
| DS 2 | 9.83 | 0.99 | 1.40 |
| DS 3 | 3.76 | 1.39 | 1.84 |
| DS 4 | >6 | 1.17 | 1.20 | n.c. = not carried out.

In the following Table II are given, in an analogous way, the results of a digoxin determination with the use of a digoxin-POD conjugate which, in one case, were achieved with native POD and, in the other case, with POD treated according to the present invention. For comparison, there was carried out an RIA test with radioactively-labelled digoxin. Conjugate III is according to the present invention and conjugate IV does not contain treated POD. The results give found ng. of digoxin per ml.

TABLE II

| control serum | dig. RIA | conjugate III | conjugate IV |
|---|---|---|---|
| serum 1 | <0.5 | 0.38 | 1.76 |
| serum 2 | <0.5 | 0.43 | 0.94 |
| serum 3 | <0.5 | 0.43 | 0.81 |
| serum 4 | 0.5 | 0.36 | 1.65 |
| serum 5 | 0.85 | 0.86 | 3.53 |
| serum 6 | <0.5 | 0.41 | 1.39 |
| serum 7 | <0.5 | 0.40 | 1.20 |

The above values show that with a POD conjugate prepared according to the present invention, results are obtained which correspond to the results obtained according to the RIA method, whereas conjugates with POD not treated according to the present invention give, in part, considerable deviations from the correct value. Analogous results are achieved with other labelling enzymes which contain a carbohydrate part in the molecule.

By means of the present invention, the precision and dependability of enzyme immuno determinations with the use of carbohydrate-containing labelling enzymes is distinctly improved and the provision of test reagents is made possible which, with an enzyme labelling, achieve just as dependable results as with radioactive-labelling and thus make unnecessary the use of radioactive substances and the safety precautions involved therewith.

The following Examples are given for the purpose of illustrating the present invention:

EXAMPLE 1

Preparation of digoxigenin-POD.

(A) Oxidation and reduction of POD.

10 mg. commercially available POD in 1.5 ml. double distilled water (pH 5.0) are mixed at 0° C. with 0.2 ml. 0.2 mole/liter sodium periodate (42 mg./ml. in double distilled water).

After 40 minutes, the solution is desalinated by means of a molecular sieve (Sephadex G-25) in 10 mmole/liter acetate (pH 5.0).

The protein-containing fractions are combined and cooled to 0° C.

With 1 mole/liter carbonate/bicarbonate (pH 9.0), the pH is adjusted to 8.0 and immediately, while stirring, sodium borohydride is added to 20 mmole/liter ($\stackrel{\wedge}{=} 0.756$ mg./ml.).

After 30 minutes, the pH is adjusted to 8.5. The solution is then further stirred for 2 hours at 0° C., followed by dialysis against 0.1 mole/liter potassium phosphate buffer (pH 8.0). The product (POD(ox)) is, if necessary, chromatographed on Sephacryl S-200 in 0.1 mole/liter phosphate buffer (pH 8.0).

(B) 200 mg. of the product (POD(ox)) obtained according to A) in 20 ml. 0.2 mole/litre potassium phosphate buffer (pH 8.0) are cooled to 4° C.

73 mg. Digoxigenin-succinyl-OSu (OSu=hydroxysuccinimide) are dissolved in 5 ml. anhydrous ethanol and introduced at 4° C., in one portion, into the POD solution, followed by gentle stirring for 16 hours at 4° C.

The batch is thereafter (without noteworthy activity loss) dialysed against 0.1 mole/liter potassium phosphate buffer (pH 8.0)/0.15 mole/liter sodium chloride.

The purification of the batch is carried out on a 50 ml. phenylsepharose column, the column being equilibrated with 0.1 mole/liter potassium phosphate buffer (pH 8.0)/0.15 mole/liter sodium chloride. From the beginning of the absorption of the retentate, the run-off of the column is fractionated at a rate of 150 ml./hour. After absorption of the crude conjugate, further elution is carried out with the equilibration buffer at the same flow. After about 50 to 55 ml. volume in the flow-through, the column eluate is combined and the conjugate pool formed with a volume of 50 to 55 ml. The conjugate pool contains about 50% of the POD activity introduced. The pool is concentrated by ultrafiltration to about 10 mg. conjugate/ml. corresponding to about 10 KU/ml.

EXAMPLE 2

Preparation of T$_3$-POD.

100 mg. POD(ox), prepared according to Example 1 (A), in 0.1 mole/l. potassium phosphate buffer (pH 8.0) are mixed at 0° C. with 9.4 ml. dimethylformamide (DMF). 25 mg. BOC-T3-OSu (BOC=tert.-butoxycarbonyl) in 0.6 ml. DMF are added at 0° C. and the reaction continued for a further 18 hours, while stirring, all the steps being protected against light.

Subsequently, dialysis is carried out against 40 mmole/liter tris/HCl buffer (pH 7.5)/0.15 mole/liter sodium chloride at 4° C. The retentate is applied to 80 ml. phenylsepharose (column diameter 3 cm.) in 40 mmole/liter tris/HCl buffer (pH 7.5)/0.15 mole/liter sodium chloride, equilibrated with 1 CV/hour (CV =column volume). Unreacted POD runs through. After the achievement of the initial extinction, the 40 mmole/liter tris/HCl (pH 7.5)/0.15 mole/liter sodium chloride buffer is replaced by 50% ethylene glycol.

The tris (pH 7.5)/1 mole/liter sodium chloride and conjugate are eluted with 1 CV/hour.

The conjugate peak is pooled and the solution mixed at 4° C. with 50% of the conjugate volume of 0.5 mole/liter hydroxylamine hydrochloride solution (pH 7.0) and stirred for 2 hours.

Dialysis is then carried out against 40 mmole/liter potassium phosphate buffer (pH 6.5) at 4° C., while protected against light. The conjugate is concentrated to c=10 mg./ml. and made up with bovine serum albumin (BSA) to c=5 mg./ml.

EXAMPLE 3
Preparation of $T_4$-POD.

10 mg. POD(ox), prepared according to Example 1 (A), in 1 ml. 0.1 mole/liter potassium phosphate buffer (pH 8.5) are slowly mixed with 0.94 ml. DMF at 0° C.

While cooling with ice, 2.5 mg. BOC-$T_4$-OSu in 60 $\mu$l. DMF are added and the batch stirred for 6 hours at 25° C. Thereafter, dialysis is carried out against 40 mmole/liter tris/HCl buffer (pH 7.5)/0.15 mole/liter sodium chloride.

The dialysate is purified on phenylsepharose in 40 mmole/liter tris/HCl buffer (pH 7.5)/0.15 mole/liter sodium chloride.

4 ml. column volumes are used per 10 mg. POD. Elution is carried out with equilibration buffer at 1 CV/hour. When the initial extinction of the eluate is again achieved, the conjugate is eluted with 50% ethylene glycol in 40 mmole/liter tris/HCl buffer (pH 7.5)/0.15 mole/liter sodium chloride at 1 CV/hour.

The conjugate peak is concentrated to c=10 mg./ml. and dialysed, while protected against light, against 40 mmole/liter potassium phosphate buffer (pH 6.5) at 4° C.

The conjugate is made up to c=5 mg./ml. with BSA and stored at 4° C.

EXAMPLE 4

A digoxigenin-POD conjugate is prepared as described in Example 1 (B) but with the use of native POD. The conjugate is dialysed against double distilled water and, as described in Example 1 (A), subjected to the oxidation/reduction treatment, whereby, instead of native POD, there is used an equimolar amount of the digoxigenin/POD conjugate.

The conjugate obtained corresponds in its properties in the test completely to the conjugate obtained according to Example 1.

EXAMPLE 5

$T_3$ test 1. Incubation; immune reaction

The synthetic resin test tubes, coated with anti-$T_3$ antibodies, of the commercial test packing 'Enzymun Test $T_3$' (producer Boehringer Mannheim GmbH, Order No. 204 528) are provided with 100 $\mu$l. standard solution (concentration range 0 to 6 ng. $T_3$/ml.) or sample and each with 1 ml. $T_3$-POD conjugate solution.

There are used conjugates I and II (see Table I) with, in each case, about 6 mU POD/ml in 0.12 mole/l. barbital buffer (pH 8.6) with 0.04% ANS (8-anilinonaphthalenesulphonic acid). The reaction time is 2 hours at ambient temperature. Thereafter, the incubation mixture is sucked off, mixed once with water and again sucked off after at most 5 minutes. 2. Incubation: enzymatic indicator reaction In the time rhythm of the following photometric measurement (e.g. every 15 seconds), into each test tube is pipetted 1 ml. of the POD substrate solution (phosphate/citrate buffer 0.1 mole/liter (pH 5.0), ABTS 9.1 mmole/liter and hydrogen peroxide 1.6 mmole/litre) and incubation carried out for 1 hour at ambient temperature. Subsequently, the extinction is measured at Hg 405 nm and the sample concentration read off on a standard curve carried out in series.

We claim:

1. Process for preparation of a conjugate useful in an immunoassay comprising oxidizing a labelling enzyme containing a carbohydrate part with periodic acid or an alkali metal salt thereof in an aqueous medium to form an oxidation product, reducing said oxidation product with sodium borohydride to form a second product and coupling said second product with an immunologically effective substance to form a conjugate therebetween.

2. Process for preparation of a conjugate useful in an immunoassay comprising coupling a labelling enzyme containing a carbohydrate part to an immunologically effective substance, oxidizing said labelling enzyme with periodic acid or an alkali metal salt thereof in an aqueous medium to form an oxidation product and reducing said oxidation product with sodium borohydride.

3. The process of claim 1 or 2, wherein the oxidation is carried out at a pH value of from 4 to 8.5 in a buffered solution, with cooling.

4. The process of claim 1 or 2 wherein the reduction with sodium borohydride is carried out at a pH value of from 7.5 to 9, with cooling.

5. The process of claim 3 wherein the reduction is carried out at a pH of from 7.5 to 9, with cooling.

6. Conjugate of a labelling enzyme and an immunologically effective substance prepared according to the process of claim 1 or 2.

7. The conjugate prepared by the process of claim 1 or 2, wherein the oxidation is carried out at a pH of from 4 to 8.5 in a buffered solution, with cooling.

8. The conjugate of claim 7 wherein the reduction is carried out at a pH of from 7.5 to 9, with cooling.

9. A reagent for use in an enzyme immunoassay comprising a conjugate prepared according to the process of claim 1 or 2 and a substrate for the enzyme of said conjugate.

* * * * *